US009050461B2

(12) United States Patent
Knox

(10) Patent No.: US 9,050,461 B2
(45) Date of Patent: Jun. 9, 2015

(54) RADIOTHERAPY APPARATUS

(75) Inventor: Christopher Knox, West Sussex (GB)

(73) Assignee: Elekta AB (publ), Stockholm (SE)

( * ) Notice: Subject to any disclaimer, the term of this patent is extended or adjusted under 35 U.S.C. 154(b) by 267 days.

(21) Appl. No.: 13/517,100

(22) PCT Filed: Dec. 21, 2009

(86) PCT No.: PCT/EP2009/009178
§ 371 (c)(1),
(2), (4) Date: Jun. 19, 2012

(87) PCT Pub. No.: WO2011/076227
PCT Pub. Date: Jun. 30, 2011

(65) Prior Publication Data
US 2012/0257711 A1    Oct. 11, 2012

(51) Int. Cl.
*H05G 1/58*    (2006.01)
*A61N 5/10*    (2006.01)

(52) U.S. Cl.
CPC ....... *A61N 5/1049* (2013.01); *A61N 2005/1054* (2013.01); *A61N 2005/1061* (2013.01)

(58) Field of Classification Search
CPC ........ A61B 6/00; A61B 6/032; A61B 6/4014; A61B 6/4028; G01N 23/04; G01N 23/046; G21K 5/04; G21K 5/10; A61N 2005/1061; A61N 5/10; H05G 1/70; H05G 1/58; H05G 1/56
USPC .............................. 378/9, 62, 64, 65, 92, 116
See application file for complete search history.

(56) References Cited

U.S. PATENT DOCUMENTS

| 6,842,502 B2 * | 1/2005 | Jaffray et al. ................... 378/65 |
| 2004/0024300 A1 | 2/2004 | Graf ............................... 600/407 |
| 2006/0064008 A1 * | 3/2006 | Moore .......................... 600/425 |

FOREIGN PATENT DOCUMENTS

WO    WO 2006030181 A1    3/2006    ............... A61B 6/03

OTHER PUBLICATIONS

European Patent Office, Officer Rodriguez Cossio, J., International Search Report and Written Opinion, PCT/EP2009/009178, date of mailing Mar. 31, 2010, 12 pages.
Ceusan, *Scattered and Leakage Radiation During Radiotherapy Treatments*, McGill University, Medical Physics Unit Presentation, Nov. 26, 2004, 31 pages.

(Continued)

*Primary Examiner* — Jurie Yun
(74) *Attorney, Agent, or Firm* — Sunstein Kann Murphy & Timbers LLP

(57) ABSTRACT

In radiotherapy apparatus comprising an imager for the MV beam and a separate kV imaging system, it is common for there to be significant artifacts in the kV image arising from the MV pulse. We disclose such a radiotherapy apparatus which is adapted to (i) cause the therapeutic source to emit radiation while keeping the diagnostic source inactive, (ii) read an image from the detector associated with the therapeutic source, (iii) cause the diagnostic source to emit radiation and while keeping the therapeutic source inactive, (iv) read an image from the detector associated with the diagnostic source, and (v) repeat as necessary. The control unit is preferably adapted to, at steps (ii) and (iv), read an image from both of the detectors, or to clear the "inactive" detector. The detectors are ideally flat-panel detectors, capturing a two-dimensional image.

9 Claims, 2 Drawing Sheets

(56) References Cited

OTHER PUBLICATIONS

Sykes et al., *A feasibility study for image guided radiotherapy using low dose, high speed, cone beam X-ray volumetric imaging*, Radiotherapy and Oncology 77 (2005) 45-52, 8 pages.

Burridge et al., *Online Adaptive Radiotherapy of the Bladder: Small Bowel Irradiated-Volume Reduction*, Int. J. Radiation Oncology Biol. Phys., vol. 66, No. 3, pp. 892-897, 2006. 6 pages.

Moore et al., *Developments in and experience of kilovoltage X-ray cone beam image-guided radiotherapy*, The British Journal of Radiology, 79 (2006), S66—S78, 13 pages.

Marchant et al., *Image Quality of On-board Cone-beam CT Acquired during VMAT Delivery*, Proceedings of the 51st Annual ASTRO Meeting, 207, 2009, 12 pages.

* cited by examiner

RADIOTHERAPY APPARATUS

FIELD OF THE INVENTION

The present invention relates to radiotherapy apparatus.

BACKGROUND ART

Radiotherapeutic apparatus is often provided with a secondary diagnostic x-ray source in addition to the primary therapeutic source of x-rays (or other radiation). As the primary source is required to rotate around the patient in order to irradiate the target volume from a range of directions and thereby minimise the dose to healthy tissue, it is convenient to mount the diagnostic source on the same rotateable support as the primary source so that it too can rotate around the patient. In this way, the diagnostic source can produce a range of images of the patient from different directions, which can (if desired) be used to reconstruct a CT dataset.

Generally, there will be a flat panel imager associated with the secondary diagnostic source in order to capture the x-ray signal after attenuation by the patient. It is also common to provide a flat-panel detector for the therapeutic beam, to provide an image of the beam after attenuation by the patient. The two flat panel imagers will usually be somewhat different, each being suited to the different energies of the respective beams. Typically, the diagnostic beam is of a relatively lower energy (several kV), at which the attenuation coefficients of different tissue types are distinctly different and a good image with adequate contrast can be obtained. The therapeutic beam is of significantly higher energy (several MV), chosen for its therapeutic efficacy; at this energy the attenuation coefficients are more similar and such "portal" images are traditionally of poor contrast, although recent improvements in flat panel imagers has addressed this.

The result of this is that the rotateable support must carry two sources and two flat panel imagers, each opposite their associated source. Generally, this is achieved by placing the two sources at locations offset 90° from each other. Each source issues a pulse of radiation, and the associated imager receives a synchronised signal instructing it to read out an image frame. The flat panel imagers are usually of an integrating nature, i.e. each pixel output reflects the total amount of radiation that has impinged on that pixel location since the last read-out.

SUMMARY OF THE INVENTION

Thus, the MV imaging is synchronised with the MV radiation pulses, and the kV imaging is synchronised with the kV pulses. There is however no link between the MV imaging and the kV imaging. The consequence of this is that the two systems run completely independently. The effect of that is that the kV images contain significant artefacts arising from the MV pulse; some of the scatter from the MV pulse exits the patient at about 90° and impinges on the kV detector. If the MV imager is sufficiently sensitive, it may also be affected by scatter from the kV source.

The present invention therefore provides a radiotherapy apparatus, comprising a source of therapeutic radiation adapted to irradiate a spatial volume, and an associated detector located on an opposite side of the spatial volume relative to the therapeutic source, to capture an image of the radiation as attenuated by objects in the spatial volume, a source of diagnostic radiation, having an energy less than that of the therapeutic radiation, adapted to irradiate the same spatial volume from a different direction, and an associated detector located on an opposite side of the spatial volume relative to the diagnostic source, to capture an image of the radiation as attenuated by objects in the spatial volume, and a control unit for the sources and the detectors, the control unit being adapted to (i) cause the therapeutic source to emit radiation and the diagnostic source to remain inactive, (ii) read an image from the detector associated with the therapeutic source, (iii) cause the diagnostic source to emit radiation and the therapeutic source to remain inactive, (iv) read an image from the detector associated with the diagnostic source, and (v) repeat as necessary.

In this way, undesirable artefacts in the one or both images arising from the other beam are eliminated. This can be used to improve the quality of the images, or to increase the aperture size of one or both beams, or some combination of the two.

The sources and the detectors will usually be rotateable around the spatial volume as discussed above. Likewise, the direction of irradiation of the spatial volume by the therapeutic source is preferably orthogonal to the direction of irradiation of the spatial volume by the diagnostic source.

The control unit is preferably adapted to, at steps (ii) and (iv), read an image from both of the detectors. In most detectors, the step of reading an image also clears the (integrating) pixels, and therefore any scatter image data that has accumulated since the last (useful) image will be cleared by this step. The image read in this way can be simply discarded.

Alternatively, if the imager has a "clear" or reset instruction, then the control unit can be adapted at step (ii) also to clear any acquired image data from the detector associated with the diagnostic source, and at step (iv) also to clear any acquired image data from the detector associated with the therapeutic source.

The detectors are ideally flat-panel detectors, capturing a two-dimensional image. Other forms of detector could alternatively be provided, such as scintillator & camera devices.

As noted above, the sources and the detectors are preferably mounted on a rotateable support, the axis of rotation of which passes through the spatial volume.

DESCRIPTION OF THE DRAWINGS

An embodiment of the present invention will now be described by way of example, with reference to the accompanying figures in which.

DETAILED DESCRIPTION OF THE EMBODIMENTS

Figure 1:
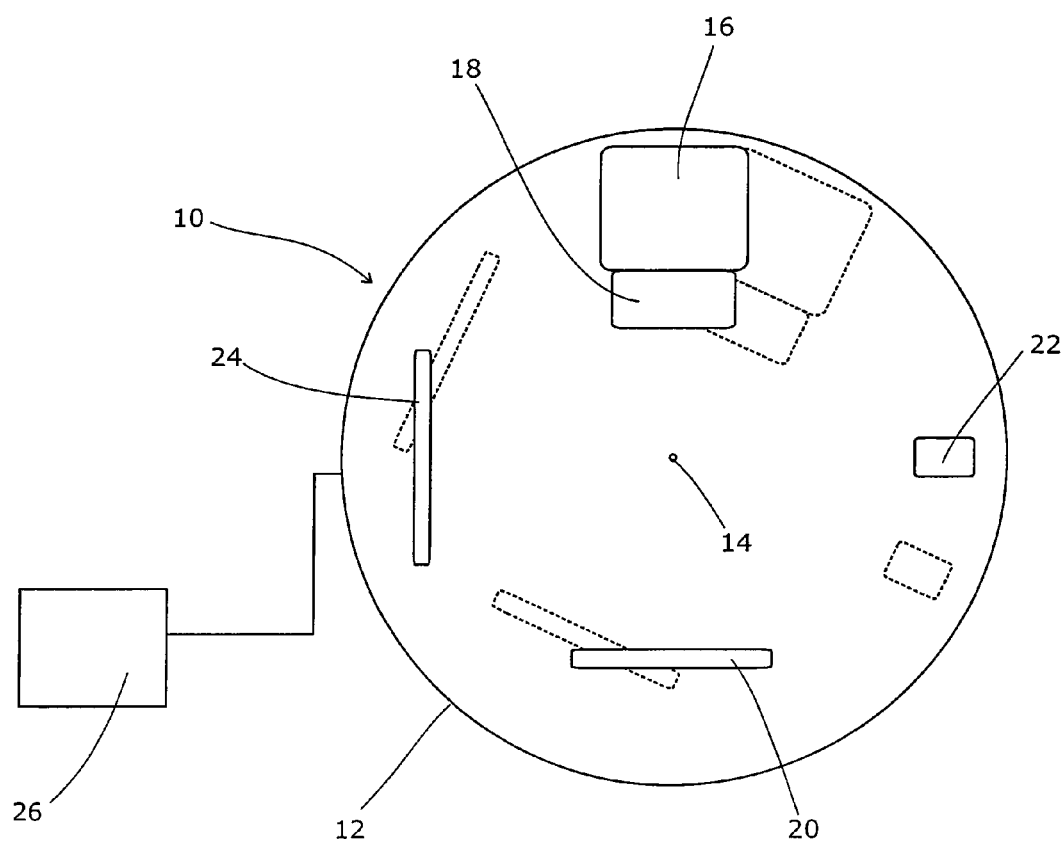
FIG. 1 shows a radiotherapy apparatus according to the present invention.

Referring to FIG. 1, a radiotherapy apparatus 10 comprises a rotateable support 12 which is generally circular and mounted on a suitable substantial base, such as an internal wall of the building in which the apparatus is located. An arrangement of bearings and drives allows the support to rotate around a central horizontal axis 14 in a generally known manner.

A linear accelerator is built into the support 12 and extends forward from the support at an off-centre position, ending in a source of megavoltage therapeutic X-radiation 16 directed radially inwardly towards the rotation axis 14. Collimation apparatus 18 is provided on the source 16, in a generally known manner so as to shape the beam as required. Thus, a patient can be supported with a target region located approximately at the point of intersection of the rotational axis 14 and the beam emitted by the source 16 (known as the "isocentre") and the tumour will be irradiated. The support 12 can then be rotated, allowing the source 16 to irradiate the patient from a variety of directions. In this way, the dose to the target region can be maximised whilst minimising the dose to the surrounding healthy tissue.

A megavoltage imaging panel 20 is provided, supported on a rotateable support 12 diametrically opposite the MV source 16. This captures an image from the radiation emitted by the source 16 as attenuated by the patient and can provide useful information as to the internal structure of the patient.

Historically, the MV image obtained in this way has been of generally poor contrast, and therefore many radiotherapy apparatus also include a diagnostic kV source 22. This is also mounted on the rotateable support 12, typically located 90 degrees away from the MV source 16. Collimation can be provided for this source, usually static in order to limit the beam to the desired aperture size. A corresponding flat panel two-dimensional kV imaging panel 24 is also provided, diametrically opposite the kV source 22.

A control unit 26 serves to control the radiation sources 16, 22, the collimator 18, the flat panel imagers 20, 24, the support 12, and other equipment that may be provided as required. One specific task of the control unit 26 is to issue timing signals dictating when irradiation pulses are issued and when the flat panel images are read.

Figure 2:
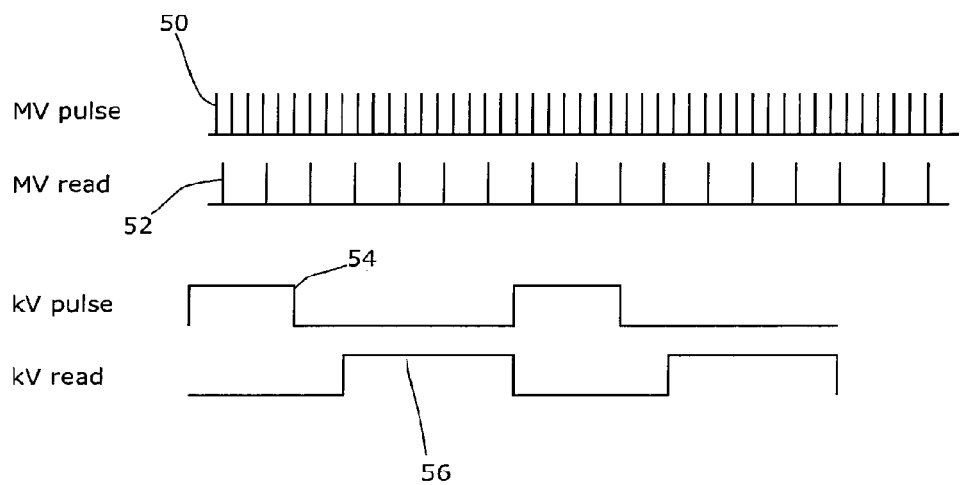
FIG. 2 shows a known timing scheme.

The typical timing patterns for known apparatus of this type are illustrated in FIG. 2. In such a timing scheme, each source/imager pair operates independently. The MV source issues a series of pulses 50, and the MV imaging panel receives periodic imaging signals 52. As illustrated, a read signal is issued after every few radiation pulses, but this is not universal and (alternatively) there may be several read signals between each pulse (for example). On receipt of each imaging signal 52, the panel reads out the accumulated intensity for each pixel within the next line or lines of the panel to be read; this corresponds to the amount of radiation received at each pixel since the last read command. After a series of imaging signals 52, the panel will have read out a complete frame, at which point it begins again at the first line. Likewise, the kV source issues bursts of radiation 54, in between which there are read signals 56 which usually prompt the readout of a complete frame (i.e. a 2D image). This arrangement leads to the difficulties described above.

Figure 3:
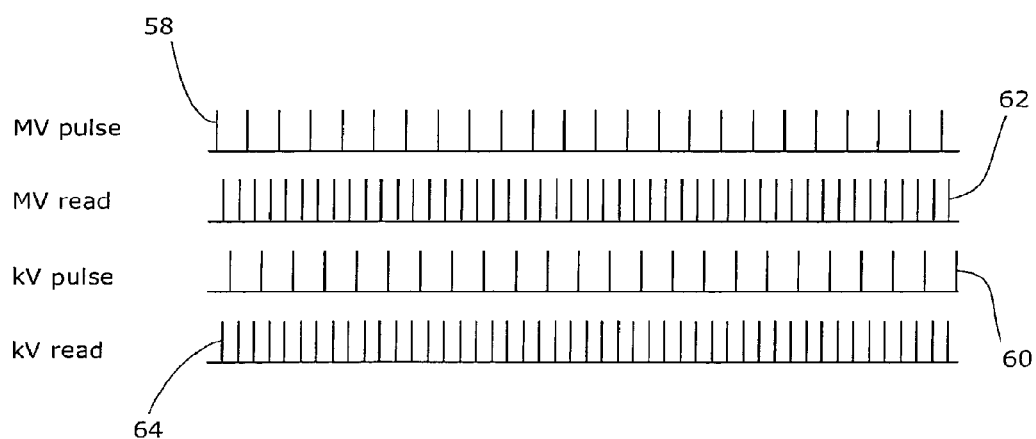
FIG. 3 shows a timing scheme according to the present invention.

According to this embodiment of the invention, a timing scheme as set out in FIG. 3 is employed. The MV source issues pulses 58 on a periodic basis as dictated by the dosage called for in the treatment plan (or otherwise). Between these MV pulses 58, the kV source issues pulses 60, at approximately the same frequency but out of step with the MV pulses 58. Meanwhile, both imaging panels receive (respectively) MV imaging signals 62 and kV imaging signals 64, substantially simultaneously.

Each "read" signal 62 or 64 does also acts to clear the panel of any data accumulated since the last read signal and thus also acts as a "clear" signal. It will be noted that half of the above "read" signals will yield an image for which there has been no imaging pulse. These images are discarded, thus keeping only the read output of the MV panel that follows immediately after an MV pulse 58 and the read output of the kV panel that forms immediately after a kV pulse 60.

Alternatively, some imaging panels provide a "clear" signal, and in such arrangements a "clear" signal could be sent alternating with a read signal 62 or 64 in line with the above scheme.

The result of this process is that an MV pulse 58 is issued, and the MV panel is read whilst the kV panel is cleared. A kV pulse is then issued, following which the MV panel is cleared and the kV panel is read. The process then repeats. In this way, scattering of (principally) the MV radiation to reach the kV panel does not cause artefacts because, although the kV panel will record such artefacts, they will be cleared prior to performing an image that is used.

The advantages of this invention could be used in a number of ways. First, the kV image will be substantially cleaner and may be used to create better quality images and/or better quality CT data sets, and/or to increase the aperture of one or both radiation sources without having as detrimental an effect in the image quality as would otherwise be the case. Alternatively, or in addition, the MV image created in this way can be used as an alternate data set to supplement the kV data set; by rotating the support 12 through 90 degrees around the patient, a full 180 degree sweep of images can be obtained (assuming that the MV and kV sources are separated by 90 degrees). In practice, the gantry may need to be rotated by an additional amount corresponding to whatever cone angle is employed. A combined reconstruction could then be created from the two sets of artefact-free images.

It will of course be understood that many variations may be made to the above-described embodiment without departing from the scope of the present invention.

The invention claimed is:

1. Radiotherapy apparatus comprising:
   a source of therapeutic radiation adapted to irradiate a spatial volume, and an associated detector located on an opposite side of the spatial volume relative to the therapeutic source, to capture an image of the radiation as attenuated by objects in the spatial volume;
   a source of diagnostic radiation, having an energy less than that of the therapeutic radiation, adapted to irradiate the same spatial volume from a different direction, and an associated detector located on an opposite side of the spatial volume relative to the diagnostic source, to capture an image of the radiation as attenuated by objects in the spatial volume, and
   a control unit for the sources and the detectors; the control unit being adapted to:
   i. cause the therapeutic source to emit radiation and the diagnostic source to remain inactive,
   ii. read an image from the detector associated with the therapeutic source,
   iii. cause the diagnostic source to emit radiation and the therapeutic source to remain inactive,
   iv. read an image from the detector associated with the diagnostic source.

2. Radiotherapy apparatus according to claim 1 in which the sources and the detectors are rotatable around the spatial volume.

3. Radiotherapy apparatus according to claim 1 in which the direction of irradiation of the spatial volume by the therapeutic source is orthogonal to the direction of irradiation of the spatial-volume by the diagnostic source.

4. Radiotherapy apparatus according to claim 1 in which the control unit is adapted at steps (ii) and (iv) to read an image from both of the detectors.

5. Radiotherapy apparatus according to claim 1 in which the control unit is adapted at step (ii) also to clear any acquired image data from the detector associated with the diagnostic source, and at step (iv) also to clear any acquired image data from the detector associated with the therapeutic source.

6. Radiotherapy apparatus according to claim 1 in which the control unit is adapted to repeat steps (i) to (iv) a plurality of times.

7. Radiotherapy apparatus according claim 1 in which the detectors are flat-panel detectors.

8. Radiotherapy apparatus according to claim 1 in which the sources and the detectors are mounted on a rotatable support, the axis of rotation of which passes through the spatial volume.

9. Radiotherapy apparatus according to claim 1 in which the control unit is adapted at step (iii) to clear any acquired image data from the detector associated with the diagnostic source prior to causing the diagnostic source to emit radiation.

* * * * *